(12) United States Patent
Hamada et al.

(10) Patent No.: US 8,674,130 B2
(45) Date of Patent: Mar. 18, 2014

(54) PROCESSES FOR PRODUCTION OF CYCLIC ALKYLENE PHOSPHOROHALIDITE AND CYCLIC PHOSPHORIC ACID ESTER

(75) Inventors: Toshiya Hamada, Osaka (JP); Sakiko Hamada, Osaka (JP)

(73) Assignee: Daihachi Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 13/497,955

(22) PCT Filed: Sep. 21, 2010

(86) PCT No.: PCT/JP2010/066322
§ 371 (c)(1),
(2), (4) Date: Apr. 27, 2012

(87) PCT Pub. No.: WO2011/040287
PCT Pub. Date: Apr. 7, 2011

(65) Prior Publication Data
US 2012/0264965 A1    Oct. 18, 2012

(30) Foreign Application Priority Data

Oct. 1, 2009  (JP) ................................. 2009-229622

(51) Int. Cl.
*C07F 9/09* (2006.01)
(52) U.S. Cl.
USPC .................................. 558/79; 558/70; 558/73
(58) Field of Classification Search
USPC ..................... 558/70, 73, 76, 78, 79
See application file for complete search history.

(56) References Cited

U.S. PATENT DOCUMENTS

| | | | |
|---|---|---|---|
| 4,112,014 A | 9/1978 | Smith et al. | |
| 5,225,467 A | 7/1993 | Ahluwalia et al. | |
| 5,424,348 A | 6/1995 | Mahood | |
| 5,919,966 A * | 7/1999 | Marlin | 558/78 |
| 6,127,464 A | 10/2000 | Tokuyasu et al. | |
| 7,728,162 B2 * | 6/2010 | Fujimoto et al. | 558/73 |
| 7,745,655 B1 | 6/2010 | Borgmann | |
| 2009/0062554 A1 | 3/2009 | Fujimoto et al. | |
| 2009/0062568 A1 | 3/2009 | Kyoda et al. | |

FOREIGN PATENT DOCUMENTS

| | | |
|---|---|---|
| JP | 58-192894 | 11/1983 |
| JP | 02-273688 | 11/1990 |
| JP | 05-239264 | 9/1993 |
| JP | 8-176172 | 7/1996 |
| JP | 10-101687 | 4/1998 |
| JP | 11-181428 | 7/1999 |
| JP | 2001-220395 | 8/2001 |
| JP | 2005-527520 | 9/2005 |
| WO | 2006/049010 | 5/2006 |
| WO | 2006/049011 | 5/2006 |

OTHER PUBLICATIONS

Search report from PCT/JP2010/066322, mail date is Nov. 2, 2010.

* cited by examiner

*Primary Examiner* — Golam M M Shameem
(74) *Attorney, Agent, or Firm* — Greenblum & Bernstein, P.L.C.

(57) ABSTRACT

A process for producing a cyclic alkylene phosphorohalidite, which comprises reacting a specific phosphorus trihalide with a specific alkylene glycol compound under conditions where the phosphorus trihalide is present in an excess amount relative to the amount of the alkylene glycol compound in the reaction system to order to obtain the cyclic alkylene phosphorohalidite by reacting the alkylene glycol compound with the phosphorus trihalide; and a process for producing a cyclic phosphoric acid ester by using the obtained cyclic alkylene phosphorohalidite as a raw material.

9 Claims, No Drawings

PROCESSES FOR PRODUCTION OF CYCLIC ALKYLENE PHOSPHOROHALIDITE AND CYCLIC PHOSPHORIC ACID ESTER

TECHNICAL FIELD

The present invention relates to a process for producing a cyclic alkylene phosphorohalidite containing an extremely small amount of a compound having a halogen directly attached to a carbon atom of the compound and a process for producing a cyclic phosphoric acid ester having an extremely low halogen content using the cyclic alkylene phosphorohalidite obtained by the aforementioned process as a raw material.

BACKGROUND ART

Generally, halogens are known as environmental toxins, and therefore industrial materials are made progressively halogen-free. In particular, there has been an increased demand for halogen-free materials in the field of office automation equipments, and most housings of personal computers, printers and the like are made progressively halogen-free.

Some material fields independently create halogen-free standards; for example, the Japan Electronics Packaging Circuits Association defines a printed circuit board containing "900 ppm or less of bromine, 900 ppm or less of chlorine, and 1500 ppm in total of bromine and chlorine" as halogen-free (JPCA-ES01-2003).

Meanwhile, expanded polyurethane foam is more difficult to be made flame-retardant than other resin materials, and therefore halogen compounds and halogen-containing phosphoric acid ester compounds that are highly effective as flame retardants have been used so far. With the current preference for halogen-free materials, however, the tendency has been to voluntarily shift to halogen-free flame retardants.

In order to be halogen-free, a flame retardant is required to have a halogen content of an added resin material comparable to or lower than the above-mentioned definition of the halogen-free printed circuit board.

In the meantime, phosphoric acid esters are known as useful chemical substances in a wide range of fields in the chemical industry as additives for resins such as flame retardants and plasticizers and as materials or intermediates of pharmaceutical products and the like.

In particular, it is known that a phosphoric acid ester having a cyclic alkylene skeleton delivers superior performance as a flame retardant because of its characteristic structure. For example, Japanese Unexamined Patent Publication No. HEI 11(1999)-181428 (Patent Document 1) discloses that a phosphoric acid ester having a phosphorinane skeleton is useful as a flame retardant for polyurethane resin.

In addition, phosphorous acid esters having a cyclic alkylene skeleton are generally useful chemical substances in a wide range of fields in the chemical industry, being widely used not only as intermediates of the above-mentioned phosphoric acid esters but also as stabilizers of resins and various kinds of compounds.

For example, Japanese Unexamined Patent Publication No. HEI 5(1993)-239264 (Patent Document 2) discloses that 5,5-dimethyl-2-nonylphenoxy-1,3,2-dioxaphosphorinane can be used as a stabilizer of cellulose ester resin and effectively prevent discoloration of the polymer and deterioration of physical properties due to a lowered degree of polymerization of the ester resin.

Cyclic alkylene phosphorohalidites are used as intermediates in production of the above-mentioned phosphoric acid esters or phosphorous acid esters having a cyclic alkylene skeleton and generally obtained through a reaction between a phosphorus trihalide and an alkylene glycol compound.

For example, Japanese Unexamined Patent Publication No. HEI 2(1990)-273688 (Patent Document 3) discloses that phosphorus trichloride is added to and reacted with neopentyl glycol under ice cooling to obtain 5,5-dimethyl-2-chloro-1,3,2-dioxaphosphorinane.

The pamphlet of WO 2006/049010 (Patent Document 4) discloses a method for producing a phosphonate having an alcoholic hydroxy group by addition reaction of a phosphite having two substituents with a carbonyl compound in the presence of a nitrogen-containing basic compound and a metal halide; and the pamphlet of WO 2006/049011 (Patent Document 5) discloses a method for producing a phosphorus compound having a phosphate-phosphonate bond by subjecting a phosphonate having an alcoholic hydroxy group and a di-substituted phosphorohalidite to a dehydrohalogenation reaction in the presence of a nitrogen-containing basic compound, and oxidizing the resulting reaction product with hydrogen peroxide, for example.

RELATED ART DOCUMENTS

Patent Documents

[Patent Document 1] Japanese Unexamined Patent Publication No. 11(1999)-181428
[Patent Document 2] Japanese Unexamined Patent Publication No. HEI 5(1993)-239264
[Patent Document 3] Japanese Unexamined Patent Publication No. HEI 2(1990)-273688
[Patent Document 4] Pamphlet of WO 2006/049010
[Patent Document 5] Pamphlet of WO 2006/049011

SUMMARY OF THE INVENTION

Problems to be Solved by the Invention

When a halidite obtained by the reaction between neopentyl glycol and phosphorus trichloride disclosed in Patent Document 3 is used to synthesize a phosphoric acid ester, the halogen concentration of the phosphoric acid ester is high to cause inconvenience to reduction of halogen content of a final product (to production of halogen-free product).

The inventors of the present invention have made intensive studies on causes of an increased halogen concentration in a phosphoric acid ester and, as a result, found that a large amount of halogenated alcohol (compound having a halogen directly attached to a carbon atom) is generated as a by-product in production of a halidite, and when a phosphoric acid ester is produced by using the halidite, the halogenated alcohol changes into a compound such as a halogenated phosphoric acid ester that is difficult to remove in a purification step. However, if the halidite is to be purified to remove the halogenated alcohol, the process will be complicated and the yield may be reduced.

In addition to the halogenated alcohol, a phosphite may be generated as a by-product, and the phosphite may become an acid phosphate through air oxidation to cause reduction of the product quality and reduction of the yield.

However, Patent Document 3 does not disclose the generation of such halogenated alcohol as a by-product or the halogen concentration in the phosphoric acid ester, or describe it as a problem.

It is therefore an object of the present invention to provide a process for producing a cyclic alkylene phosphorohalidite containing an extremely small amount of compound having a halogen directly attached to a carbon atom and a method for producing a cyclic phosphoric acid ester having an extremely low halogen content using the cyclic alkylene phosphorohalidite obtained by the aforementioned process as a raw material.

Means for Solving the Problems

The inventors of the present invention have made intensive studies to solve the above-described problems and, as a result, found that when a phosphorus trihalide is present in an excess amount in a system of reaction between the phosphorus trihalide and an alkylene glycol compound in production of a cyclic alkylene phosphorohalidite, it is possible to inhibit generation of a compound having a halogen directly attached to a carbon atom; and that when a cyclic alkylene phosphorohalidite produced under the above-described condition is used for an intermediate material, it is possible to produce a cyclic phosphoric acid ester having an extremely low halogen content, to reach completion of the present invention.

The present invention therefore provides a process for producing a cyclic alkylene phosphorohalidite, comprising reacting an alkylene glycol compound represented by the general formula (II):

HO—R⁰—OH (II)

wherein $R^0$ is a linear or branched alkylene group having 2 to 20 carbon atoms or a cyclic alkylene group having 3 to 20 carbon atoms, with a phosphorus trihalide represented by the general formula (III):

PX₃ (III)

wherein X is a halogen atom,
to obtain the cyclic alkylene phosphorohalidite being represented by the general formula (I):

[Formula 1]

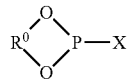

(I)

wherein $R^0$ and X are as defined above,
the phosphorus trihalide and the alkylene glycol compound being reacted under conditions where the phosphorus trihalide is present in an excess amount relative to the amount of the alkylene glycol compound in the reaction system.

The present invention also provides a process for producing a cyclic phosphoric acid ester by using the above-described cyclic alkylene phosphorohalidite as a raw material.

Effects of the Invention

The present invention can provide a process for producing a cyclic alkylene phosphorohalidite containing an extremely small amount of compound having a halogen directly attached to a carbon atom and a process for producing a cyclic phosphoric acid ester having an extremely low halogen content by using the cyclic alkylene phosphorohalidite obtained by the aforementioned process as a raw material.

That is, by using the cyclic alkylene phosphorohalidite obtained by the production process of the present invention as an intermediate, it is possible to produce a cyclic phosphoric acid ester having an extremely low halogen content to deserve to be referred to as a halogen-free compound in the fields of various industrial materials.

MODE FOR CARRYING OUT THE INVENTION

The process for producing a cyclic alkylene phosphorohalidite of the present invention comprises reacting an alkylene glycol compound represented by the general formula (II) with a phosphorus trihalide represented by the general formula (III) to obtain a cyclic alkylene phosphorohalidite represented by the general formula (I), characterized in that the phosphorus trihalide and the alkylene glycol compound are reacted under conditions where the phosphorus trihalide is present in an excess amount relative to the amount of the alkylene glycol compound in the reaction system.

That is, the present invention is characterized in that the phosphorus trihalide and the alkylene glycol compound are reacted in a reaction system where the phosphorus trihalide is present in an excess amount, and it is thereby possible to inhibit generation of a compound having a halogen directly attached to a carbon atom as a by-product to obtain a cyclic alkylene phosphorohalidite containing an extremely small amount of the compound. By using the cyclic alkylene phosphorohalidite as an intermediate material, it is possible to obtain a cyclic phosphoric acid ester having less impurities and an extremely low halogen content.

Hereinafter, the present invention will be described in order of reaction.
(Production of Cyclic Alkylene Phosphorohalidite)

In the production of a cyclic alkylene phosphorohalidite, a phosphorus trihalide and an alkylene glycol compound are reacted under conditions where the phosphorus trihalide is present in an excess amount relative to the amount of the alkylene glycol in the reaction system.

The conditions do not need to be maintained from initiation to completion of the reaction, but the longer the phosphorus trihalide is present in an excess amount relative to the amount of the alkylene glycol compound in the reaction system during the time between initiation and completion of the reaction, the more effective the inhibition of generation of a compound having a halogen directly attached to a carbon atom as a by-product is. It is therefore preferable to maintain the conditions where the phosphorus trihalide is present in an excess amount from initiation of the reaction till late in the reaction, and it is more preferable to maintain the conditions where the phosphorus trihalide is present in an excess amount from initiation of the reaction to completion of the reaction thoroughly.

For example, may be mentioned a method in which the whole amount of the phosphorus trihalide to use is added to the reaction system, and then the alkylene glycol compound is gradually added thereto to react the compounds; and a method in which both the compounds are added to the reaction system so that the phosphorus trihalide is always present in the reaction system in an excess amount while the reaction is taking place, of which the former is preferable in terms of workability.

The alkylene glycol compound to be used in the present invention is represented by the general formula (II):

HO—R⁰—OH (II)

wherein $R^0$ is a linear or branched alkylene group having 2 to 20 carbon atoms or a cyclic alkylene group having 3 to 20 carbon atoms.

In terms of easier formation of the cyclic alkylene phosphorohalidite and stability of the cyclic alkylene phosphorohalidite after cyclic structure formation, alkylene glycols having 2 to 4 carbon atoms in a moiety that is involved directly in the cyclic structure formation are preferable, ethyleneglycols and 1,3-propanediols are more preferable, and 1,3-propanediols having 3 carbon atoms in a linear moiety represented by the general formula (IV) is particularly preferable:
[Formula 2]

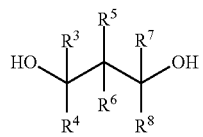

(IV)

wherein $R^3$, $R^4$, $R^5$, $R^6$, $R^7$ and $R^8$ are each independently a hydrogen atom, or a linear alkyl group having 1 to 5 carbon atoms or a branched alkyl group having 3 to 5 carbon atoms.

Examples of the alkylene glycol compound include ethylene glycol, propylene glycol (1,2-propanediol), 1,3-propanediol, neopentyl glycol (2,2-dimethyl-1,3-propanediol), 2,2-diethyl-1,3-propanediol, 2,2-dipropyl-1,3-propanediol, 2,2-dibutyl-1,3-propanediol, 2,2-dipentyl-1,3-propanediol, 2,2-dihexyl-1,3-propanediol, 2,2-diheptyl-1,3-propanediol, 2,2-dioctyl-1,3-propanediol, 2-ethyl-2-methyl-1,3-propanediol, 2-methyl-2-propyl-1,3-propanediol, 2-butyl-2-methyl-1,3-propanediol, 2-methyl-2-pentyl-1,3-propanediol, 2-ethyl-2-propyl-1,3-propanediol, 2-butyl-2-ethyl-1,3-propanediol, 2-ethyl-2-pentyl-1,3-propanediol, 2-butyl-2-propyl-1,3-propanediol, 2-pentyl-2-propyl-1,3-propanediol, 2-butyl-2-pentyl-1,3-propanediol, 1,2-butanediol, 1,3-butanediol, 1,4-butanediol, 1,2-pentanediol, 1,3-pentanediol, 1,4-pentanediol, 1,2-cyclohexanediol and 1,2-cyclopentanediol.

Out of them, 1,3-propanediol, neopentyl glycol, 2,2-diethyl-1,3-propanediol, 2,2-dipropyl-1,3-propanediol, 2,2-dibutyl-1,3-propanediol, 2,2-dipentyl-1,3-propanediol and 2-butyl-2-ethyl-1,3-propanediol are preferable, and neopentyl glycol is particularly preferable.

These alkylene glycol compounds may be used independently, or two or more kinds thereof may be used in combination.

The phosphorus trihalide that is used in the present invention is represented by the general formula (III)

$$PX_3 \quad (III)$$

wherein X is a halogen atom.

Examples of the X include fluorine, chlorine, bromine and iodine.

As the phosphorus trihalide, phosphorus trichloride and phosphorus tribromide are preferable in terms of cost and availability, of which phosphorus trichloride is particularly preferable.

The phosphorus trihalide is used at a proportion of 0.99 to 1.15 moles, preferably 1 to 1.1 moles, and more preferably 1 to 1.05 moles with respect to 1 mole of the alkylene glycol compound.

When the proportion of the phosphorus trihalide is less than 0.99 moles, there may come a time when the alkylene glycol compound is excessive in the reaction system to cause generation of a large amount of compound having a halogen directly attached to a carbon atom such as a halogenated alcohol. On the other hand, when the proportion of the phosphorus trihalide is more than 1.15 moles, the phosphorus trihalide may remain to result in decrease of the purity of the cyclic alkylene phosphorohalidite.

In addition, some reaction apparatuses may allow loss of unreacted phosphorus trihalide through volatilization occurring at the same time as generation of noncondensable hydrogen halide gas during the reaction. In that case, the amount of the phosphorus trihalide to be lost may be calculated (assumed) to add the phosphorus trihalide so as to meet the above-specified proportion.

The reaction temperature is preferably in a range of −5° C. to 60° C., more preferably in a range of 0 to 45° C., still more preferably in a range of 0 to 20° C., and particularly preferably in a range of 5 to 20° C.

When the reaction temperature is higher than 60° C., more phosphorus trihalide may be volatilized, and a halogenated alcohol may be more likely to be generated. On the other hand, when the reaction temperature is lower than −5° C., the rate of reaction between the phosphorus trihalide and the alkylene glycol compound may be significantly reduced.

In the production process of the present invention, the reaction time may be appropriately determined so as to minimize the impact on the generation of a halogenated alcohol and facilitate safe reaction progress.

Preferably, the reaction is carried out under an inert gas atmosphere in order to prevent hydrolysis and oxidation of the phosphorus trihalide, a reaction product and the like.

Examples of the inert gas include nitrogen gas, argon gas and helium gas, among which nitrogen gas is preferable in terms of cost and workability.

During the reaction, stirring of the reaction mixture may be performed appropriately.

If the concentration of the hydrogen halide generated as a by-product in the reaction is increased, decomposition of the cyclic alkylene phosphorohalidite generated may be caused to generate a halogenated alcohol as a by-product, and it is therefore preferable to progressively discharge the by-product halogenated alcohol out of the reaction system.

To this end, the reaction may be carried out in a reaction system equipped with a hydrochloric-acid-recovering device (condenser connected with a water scrubber), for example.

It is necessary to completely react unreacted phosphorus trihalide and alkylene glycol compound after completion of the addition of the materials. The progress of the reaction can be confirmed according to the amount of the hydrogen halide discharged to the outside of the system, the amount of halogen in the system, the composition in the system and the like. When it is difficult to complete the reaction, the reaction may be controlled by temperature rising, decompression or the like.

The reaction step may be carried out in the presence of an organic solvent, if necessary.

The organic solvent is not particularly limited as long as it is inert against the materials of the reaction (phosphorus trihalide and alkylene glycol compound) and the reaction product.

Specific examples thereof include hydrocarbon solvents such as hexane, cyclohexane, heptane, octane, benzene, toluene, xylene and a petroleum spirit; halogenated hydrocarbon solvents such as chloroform, carbontetrachloride, dichloromethane, dichloroethane, trichloroethane, tetrachloroethane, chlorobenzene and dichlorobenzene, which can be removed in a following step; and ether solvents such as diisopropyl ether, dibutyl ether, 1,4-dioxane and ethylene glycol diethyl ether.

Out of them, hydrocarbon solvents are preferable in terms of ease of handling, among which toluene and xylene are more preferable.

The reaction mixture obtained as described above can be used in production of a phosphoric acid ester without the need of removing the solvent and impurities.

When it is desirable to obtain a cyclic alkylene phosphorohalidite having a higher purity, the solvent and impurities may be removed by a commonly known process. Examples of the removal process include vacuum distillation.

Preferably, the cyclic alkylene phosphorohalidite, which is the reaction mixture obtained, is a material that allows a cyclic phosphoric acid ester to be produced therefrom to have a purity of more than 90.0% and a halogen content of 750 ppm or less.

Here, the term "purity" means a purity determined by a method of (Measurement for purity of cyclic phosphoric acid ester) to be described later. The expression "to have a purity of more than 90.0%" means that the purity is "more than 90% and 100% or less". The lower limit of the purity is preferably 92.0%, and more preferably 94.0%, and the upper limit of the purity is as near to 100% by weight as possible.

The expression "to have a halogen content of 750 ppm or less" means that the halogen content is "more than 0 ppm and 750 ppm or less". The upper limit of the halogen content is preferably 700 ppm, more preferably 600 ppm, and still more preferably 500 ppm.

(Method for Producing Phosphoric Acid Ester)

By using a cyclic alkylene phosphorohalidite obtained by the production process of the present invention as a raw material, it is possible to produce a cyclic phosphoric acid ester having an extremely low halogen content.

For example, the cyclic phosphoric acid ester is obtained by reacting a cyclic alkylene phosphorohalidite with a compound having a hydroxyl group, and oxidizing the resulting reaction product (trivalent phosphorus compound).

More specifically, the following production process may be mentioned.

The process comprises: reacting the cyclic alkylene phosphorohalidite (I) obtained by the production process of the present invention and a compound having a hydroxyl group and represented by the general formula (V):

R(OH)$_n$ (V)

wherein n is an integer from 1 to 4, and R is an aliphatic residue having 1 to 8 carbon atoms or an aromatic residue having 6 to 18 carbon atoms that may have a substituent and that is represented by the following formula:

[Formula 3]

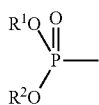

wherein R$^1$ and R$^2$ are each independently a linear alkyl group having 1 to 8 carbon atoms or a branched alkyl group having 3 to 8 carbon atoms, a cycloalkyl group having 3 to 8 carbon atoms, or an aryl group having 6 to 12 carbon atoms that may be substituted with a linear alkyl group having 1 to 4 carbon atoms or a branched alkyl group having 3 to 4 carbon atoms; or alternatively, R$^1$ and R$^2$, together with the oxygen atoms and the phosphorus atom to which they are attached, constitute a ring structure,
to obtain a reaction product represented by the general formula (VI):

[Formula 4]

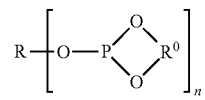 (VI)

wherein R$^0$, R and n are as defined above (step (1)); and oxidizing the reaction product to obtain a cyclic phosphoric acid ester represented by the general formula (VII):

[Formula 5]

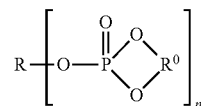 (VII)

wherein R$^0$, R and n are as defined above (step (2)).

These steps are of commonly known processes, and the reaction conditions may be determined accordingly.

(Step (1))

The substituents of the compound (V) having a hydroxyl group to be used in the present invention will be described.

Examples of the linear or branched alkyl group represented by R$^1$ and R$^2$ include methyl, ethyl, n-propyl, iso-propyl, n-butyl, iso-butyl, sec-butyl, tert-butyl, n-pentyl, iso-pentyl, 2-methylbutyl, 1,2-dimethylpropyl, neopentyl, n-hexyl, iso-hexyl, 3-methylpentyl, 2,2-dimethylbutyl, 2,3-dimethylbutyl, n-heptyl, n-octyl and 2-ethylhexyl.

Examples of the cycloalkyl group represented by R$^1$ and R$^2$ include cyclopropyl, cyclobutyl, cyclopentyl, cyclohexyl, cycloheptyl, cyclooctyl, cyclononyl and cyclodecyl.

Examples of the aryl group represented by R$^1$ and R$^2$ include phenyl, cresyl, xylyl, 1-naphthyl, 2-naphthyl and 2-phenylphenyl.

Alternatively, R$^1$ and R$^2$, together with the oxygen atoms and the phosphorus atom to which they are attached, may constitute a ring structure. The substituent —R$^1$—R$^2$— consisting of R$^1$ and R$^2$ in bond is preferably an alkylene group in which the sum of the numbers of carbon atoms contained in R$^1$ and R$^2$ is 2 to 9, and the ring in the ring structure is preferably a five- to seven-membered ring.

As the compound having a hydroxyl group, any alcohols and phenols encompassed by the general formula (V) can be used.

Examples thereof include ethanol, propanol, butanol, phenol, cresol, xylenol, phenylphenol, dibutyl(1-hydroxy-1-methylethyl)phosphonate, dibutyl(1-hydroxyethyl)phosphonate, dibutylhydroxymethylphosphonate, dicyclohexyl(1-hydroxy-1-methylethyl)phosphonate, dicyclohexyl(1-hydroxyethyl)phosphonate, dicyclohexylhydroxymethylphosphonate, diphenyl(1-hydroxy-1-methylethyl)phosphonate, diphenyl(1-hydroxyethyl)phosphonate, diphenylhydroxymethylphosphonate, ethylene glycol, 1,3-propanediol, 1,4-butanediol, trimethylolethane, trimethylolpropane and pentaerythritol.

Out of them, ethanol, propanol, butanol, phenol, cresol, xylenol, phenylphenol, dibutyl(1-hydroxy-1-methylethyl)phosphonate, dibutylhydroxymethylphosphonate, ethylene glycol, 1,3-propanediol and 1,4-butanediol are preferable.

Preferably, the cyclic alkylene phosphorohalidite and the compound having a hydroxyl group are reacted in the presence of a hydrogen halide scavenger.

Examples of the hydrogen halide scavenger include aliphatic tertiary amines such as trimethylamine, triethylamine, tripropylamine and tributylamine; aromatic amines such as aniline and toluidine; and heterocyclic amines such as pyridine, lutidine, picoline and 1,8-diazabicyclo[5,4,0]undecene-7(DBU). Out of them, triethylamine and tributylamine are preferable in terms of availability and ease of handling.

In addition, a catalyst may be used appropriately according to the reactivity of the compound having a hydroxyl group to use.

Examples of the catalyst include Lewis acids such as aluminum chloride, magnesium chloride and zinc chloride; and Bronsted acids such as sulfuric acid and p-toluenesulfonic acid. Out of them, Lewis acids are preferable in terms of catalytic activity.

The reaction step may be carried out in the presence of an organic solvent, if necessary.

The organic solvent to use is not particularly limited as log as it is inert against the materials of the reaction (compound having a hydroxyl group and cyclic alkylene phosphorohalidite), the intermediate product and the reaction product (phosphoric acid ester).

Specific examples thereof include hydrocarbon solvents such as hexane, cyclohexane, heptane, octane, toluene and xylene; halogenated hydrocarbon solvents such as chloroform, carbontetrachloride, dichloromethane, dichloroethane, chlorobenzene and dichlorobenzene; and ether solvents such as diisopropyl ether, dibutyl ether, p-dioxane and ethylene glycol diethyl ether.

Out of them, hydrocarbon solvents are preferable in terms of ease of handling, among which toluene and xylene are more preferable.

It is preferable to use the same solvent as in the production of the phosphorohalidite, because a step of collecting the solvent can be simplified.

It is also preferable to remove amine hydrohalide generated as a by-product after completion of the reaction step. As the removal process, commonly known processes such as filtration and washing in water may be employed.

(Step (2))

Subsequently, the reaction product obtained in Step (1) is oxidized by a commonly known method to obtain a phosphoric acid ester. For example, the reaction product is oxidized by a process in which hydrogen peroxide is reacted in the presence of a base.

Examples of the base to use include alkali metal hydroxides such as lithium hydroxide, sodium hydroxide and potassium hydroxide; alkali metal carbonates such as sodium carbonate and sodium hydrogen carbonate; and amines such as ammonia, dimethylamine, triethylamine and tributylamine. Out of them, sodium hydroxide and triethylamine are preferable in terms of availability.

In the present step, the same reaction vessel as in Step (1) can be continuously used.

The solvent is removed from the reaction mixture obtained as described above by a commonly known method to obtain a desired phosphoric acid ester.

In addition, impurities such as amine and acidic components may be removed by a commonly known process, if necessary. Examples of the removal process include acid washing, alkali washing, washing in water and vacuum distillation.

EXAMPLES

The present invention will be described in detail by way of the following examples and comparative examples; however, the scope of the present invention is not limited to these examples.

Example 1

To a one-liter four-necked flask equipped with a stirrer, a thermometer, a thermostat, a powder addition device, a hydrochloric-acid-recovering device (condenser connected with a water scrubber) and a reflux condenser, 137.5 g (1.0 mole, equimolar to neopentyl glycol) of phosphorus trichloride as a phosphorus trihalide and 135.2 g of toluene as a solvent were put in. The mixed solution was cooled to a temperature of 5° C. in the thermostat under a nitrogen atmosphere, and 104.0 g (1.0 mole) of neopentyl glycol as an alkylene glycol compound was gradually added thereto over 4 hours by using the powder addition device under stirring in the same condition. After completion of the addition, the resulting mixed solution was stirred and reacted in the same condition (under a nitrogen atmosphere at a temperature of 5° C.) for 1 hour to recover 69.4 g of hydrogen chloride (hydrochloric acid gas) generated by using the hydrochloric-acid-recovering device. Thereafter, the resulting reaction mixture was heated to a temperature of 40° C., the pressure in the flask was reduced to 150 torr (20 kPa), and residual hydrogen chloride was removed under stirring for 1 hour in the same condition to obtain a solution 1 containing neopentylenephosphorus chloridite as a main component.

The solution 1 obtained was used to synthesize a compound 1 to be described later, and the compound obtained was measured for the chlorine content and the purity of the cyclic phosphoric acid ester by a method to be described later.

Table 1 shows the results obtained together with the materials and the reaction conditions.

In Table 1, the ratio of the phosphorus trihalide (III) to use to the alkylene glycol compound (II) is shown as "molar ratio".

Example 2

A solution 2 containing neopentylenephosphorus chloridite as a main component was obtained in the same manner as in Example 1 except that the amount of the phosphorus trichloride to use was changed to 136.2 g (0.99 moles, less than neopentyl glycol by 1 mole %).

The solution 2 obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Example 3

A solution 3 containing neopentylenephosphorus chloridite as a main component was obtained in the same manner as in Example 1 except that the amount of the phosphorus trichloride to use was changed to 140.3 g (1.02 moles, exceeding neopentyl glycol by 2 mole %).

The solution 3 obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Example 4

A solution 4 containing neopentylenephosphorus chloridite as a main component was obtained in the same manner as in Example 1 except that the amount of the phosphorus trichloride to use was changed to 143.0 g (1.04 moles, exceeding neopentyl glycol by 4 mole %).

The solution 4 obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Example 5

A solution 5 containing neopentylenephosphorus chloridite as a main component was obtained in the same manner as in Example 1 except that the neopentyl glycol was added over 10 hours.

The solution 5 obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Example 6

A solution 6 containing neopentylenephosphorus chloridite as a main component was obtained in the same manner as in Example 1 except that the neopentyl glycol was added at a temperature of 40° C.

The solution 6 obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Example 7

A solution 7 containing 5-butyl-2-chloro-5-ethyl-1,3,2-dioxaphosphorinane as a main component was obtained in the same manner as in Example 1 except that 160.0 g (1.0 mole) of 2-butyl-2-ethyl-1,3-propanediol was used instead of the neopentyl glycol.

The solution 7 obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Comparative Example 1

To a one-liter four-necked flask equipped with a stirrer, a thermometer, a thermostat, a dropping device (funnel), a hydrochloric-acid-recovering device (condenser connected with a water scrubber) and a reflux condenser, 104.0 g (1.0 mole) of neopentyl glycol as an alkylene glycol compound and 135.2 g of toluene as a solvent were put in. The mixed solution was cooled to a temperature of 5° C. in the thermostat under a nitrogen atmosphere, and 137.5 g (1.0 mole, equimolar to neopentyl glycol) of phosphorus trichloride as a phosphorus trihalide was gradually added over 4 hours by using the dropping device under stirring in the same condition. After completion of the addition, the resulting mixed solution was stirred and reacted in the same condition (under a nitrogen atmosphere at a temperature of 5° C.) for 1 hour to recover 69.4 g of hydrogen chloride (hydrochloric acid gas) generated by using the hydrochloric-acid-recovering device. Thereafter, the resulting reaction mixture was heated to a temperature of 60° C., the pressure in the flask was reduced to 150 torr (20 kPa), and residual hydrogen chloride was removed under stirring for 1 hour in the same condition to obtain a solution 1C containing neopentylenephosphorus chloridite as a main component.

The solution 1C obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Comparative Example 2

A solution 2C containing neopentylenephosphorus chloridite as a main component was obtained in the same manner as in Comparative Example 1 except that the amount of the phosphorus trichloride to use was changed to 136.2 g (0.99 mol, less than neopentyl glycol by 1 mole %).

The solution 2C obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Comparative Example 3

A solution 3C containing neopentylenephosphorus chloridite as a main component was obtained in the same manner as in Comparative Example 1 except that the amount of the phosphorus trichloride to use was changed to 143.0 g (1.04 moles, exceeding neopentyl glycol by 4 mole %).

The solution 3C obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Comparative Example 4

A solution 4C containing neopentylenephosphorus chloridite as a main component was obtained in the same manner as in Comparative Example 1 except that the phosphorus trichloride was added over 10 hours.

The solution 4C obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Comparative Example 5

A solution 5C containing neopentylenephosphorus chloridite as a main component was obtained in the same manner as in Comparative Example 1 except that the phosphorus trichloride was added at a temperature of 20° C.

The solution 5C obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Comparative Example 6

A solution 6C containing neopentylenephosphorus chloridite as a main component was obtained in the same manner as in Example 1 except that the amount of the phosphorus trichloride to use was changed to 134.8 g (0.98 moles, less than neopentyl glycol by 2 mole %).

The solution 6C obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Comparative Example 7

A solution 7C containing neopentylenephosphorus chloridite as a main component was obtained in the same manner as in Example 1 except that the amount of the phosphorus trichloride to use was changed to 165.0 g (1.2 moles, exceeding neopentyl glycol by 20 mole %).

The solution 7C obtained was used to synthesize a compound 1 to be described later, and the compound obtained was measured for the chlorine content and the purity of the cyclic phosphoric acid ester by the method to be described later.

Table 1 shows the results obtained together with the materials and the reaction conditions.

Comparative Example 8

A reaction was attempted to be carried out in the same manner as in Example 5 except that the neopentyl glycol was added at a temperature (reaction temperature) of −10° C., but progress of the reaction that can be confirmed by generation of hydrogen chloride or the like was not observed. Due to the possibility of runaway reaction to be caused by accumulated unreacted materials, the experiment was stopped on the way.

Comparative Example 9

A reaction was attempted to be carried out in the same manner as in Example 5 except that the neopentyl glycol was added at a temperature (reaction temperature) of 70° C., but the reflux grew intense to pose dangers, and the experiment was therefore stopped on the way.

(Synthesis of Compound 1)

To a one-liter four-necked flask equipped with a stirrer, a thermometer, a thermostat, a dropping device (funnel), a hydrochloric-acid-recovering device (condenser connected with a water scrubber) and a reflux condenser, 226.8 g (0.9 moles) of dibutyl(1-hydroxy-1-methylethyl)phosphonate as an alcohol compound, 111.1 g (1.1 moles) of triethylamine as a hydrogen halide scavenger, 1.14 g (0.012 moles) of magnesium chloride as a catalyst and 20.8 g of toluene as an organic solvent were put in and stirred. The resulting mixed solution was retained at a temperature of 60° C. by using the thermostat, and the whole amount of each solution synthesized in Examples and Comparative Examples was added thereto gradually over 2 hours by using the dropping device. After completion of the addition, the resulting reaction mixture was stirred at a temperature of 60° C. for 1 hour to complete the reaction.

Subsequently, 200 g of water was added to the resulting reaction mixture. The resulting solution was stirred at a temperature of 60° C. for 30 minutes, and then was allowed to stand to be separated into phases. Then, an aqueous phase was recovered to remove triethylamine hydrochloride generated as a by-product.

Subsequently, 3.0 g (0.02 moles) of a 30% aqueous sodium hydroxide was added to the reaction mixture. The resulting solution was retained at a temperature of 20 to 60° C. by using the thermostat, and 97.1 g of a 35% hydrogen peroxide aqueous solution (1.0 mole as hydrogen peroxide) was added thereto gradually over 2 hours by using the dropping device. After completion of the addition, the resulting reaction mixture was stirred at a temperature of 60° C. for 1 hour to complete the reaction.

Then, the resulting reaction mixture was washed with an aqueous hydrochloric acid solution and a sodium carbonate aqueous solution sequentially, and finally rinsed with water. The resulting reaction mixture was heated to a temperature of 100 to 140° C., and the pressure was reduced to 100 torr (13.3 kPa) to recover water and toluene. Further, steam distillation was performed at a temperature of 100 to 140° C. under a reduced pressure of 20 torr (2.7 kPa) to remove low-boiling point components to obtain a transparent and colorless liquid (compound 1).

The liquid obtained was analyzed by gas chromatography, and the result thereof was compared with gas chromatographic analysis results of cyclic phosphoric acid esters having known cyclic structures to confirm that the main component of the liquid obtained was each of the following cyclic phosphoric acid esters.

Cyclic Phosphoric Acid Ester A

Examples 1 to 6 and Comparative Examples 1 to 7

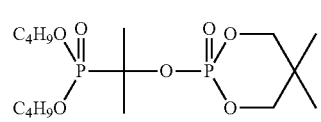

[Formula 6]

Cyclic Phosphoric Acid Ester B

Example 7

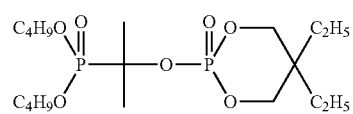

[Formula 7]

TABLE 1

|  | Example 1 | Example 2 | Example 3 | Example 4 | Example 5 | Example 6 | Example 7 |
|---|---|---|---|---|---|---|---|
| Alkylene glycol compound (II) | Neopentyl glycol | Neopentyl glycol | Neopentyl glycol | Neopentyl glycol | Neopentyl glycol | Neopentyl glycol | 2-butyl-2-ethyl-1,3-propanediol |
| Phosphorus trihalide(III) | Phosphorus trichloride | Phosphorus trichloride | Phosphorus trichloride | Phosphorus trichloride | Phosphorus trichloride | Phosphorus trichloride | Phosphorus trichloride |
| Way of addition | Alkylene glycol compound was added. | | | | | | |
| Molar ratio of phosphorus trihalide used (to compound (II)) | 1.00 | 0.99 | 1.02 | 1.04 | 1.00 | 1.00 | 1.04 |
| Time period of addition (hours) | 4 | 4 | 4 | 4 | 10 | 4 | 4 |
| Reaction temperature (° C.) | 5 | 5 | 5 | 5 | 5 | 40 | 5 |
| Amount of compound 1 obtained (g) | 348.5 | 352.8 | 348.5 | 350.6 | 349.8 | 351.4 | 394.8 |
| Purity of cyclic phosphoric acid ester (%) | 96.8 | 96.8 | 97.1 | 96.4 | 96.7 | 95.4 | 97.2 |
| Halogen content of compound 1 (ppm) | 180 | 190 | 160 | 140 | 160 | 360 | 170 |

|  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| Alkylene glycol compound (II) | Neopentyl glycol | Neopentyl glycol | Neopentyl glycol | Neopentyl glycol | Neopentyl glycol | Neopentyl glycol | Neopentyl glycol |
| Phosphorus trihalide(III) | Phosphorus trichloride | Phosphorus trichloride | Phosphorus trichloride | Phosphorus trichloride | Phosphorus trichloride | Phosphorus trichloride | Phosphorus trichloride |
| Way of addition | Phosphorus trichloride was added. | | | | | Alkylene glycol compound was added. | |
| Molar ratio of phosphorus trihalide used (to compound (II)) | 1.00 | 0.99 | 1.04 | 1.00 | 1.00 | 0.98 | 1.20 |
| Time period of addition (hours) | 4 | 4 | 4 | 10 | 4 | 4 | 4 |
| Reaction temperature (° C.) | 5 | 5 | 5 | 5 | 20 | 5 | 5 |
| Amount of compound 1 obtained (g) | 347.8 | 352.1 | 349.6 | 347.5 | 346.0 | 350.3 | 304.6 |
| Purity of cyclic phosphoric acid ester (%) | 96.6 | 97.2 | 96.5 | 96.4 | 95.6 | 96.1 | 81.3 |
| Halogen content of compound 1 (ppm) | 780 | 910 | 630 | 1400 | 1800 | 1050 | 140 |

The results shown in Table 1 have revealed the following:

(1) The halogen content of the compound 1 is remarkably reduced in Examples 1 to 7 in which the alkylene glycol compound was added to the phosphorus trihalide to carry out the reaction compared with Comparative Examples 1 to 5 in which the phosphorus trihalide was added to the alkylene glycol compound to carry out the reaction.

(2) The halogen content of the compound 1 tends to be reduced when the phosphorus trihalide is used in an excess amount relative to the amount of the alkylene glycol compound as can be seen in Examples 3 and 4, but impurities increase to reduce the purity of the desired cyclic phosphoric acid ester when the phosphorus trihalide is excessive by 20% as can be seen in Comparative Example 7.

(3) According to comparison between Example 1 and Example 5, the time period of addition of the alkylene glycol compound to the phosphorus trihalide hardly affects the halogen content of the compound 1.

(4) According to comparison between Example 1 and Example 6, the halogen content of the compound 1 tends to increase when the temperature at which the alkylene glycol compound is added to the phosphorus trihalide is raised.

(5) According to comparison between Example 1 and Example 7, the same effect of reducing the halogen content of the compound 1 can be obtained even when the neopentyl glycol as the alkylene glycol compound is replaced with the 2-butyl-2-ethyl-1,2-propanediol.

Example 8

A solution 1 containing neopentylenephosphorus chloridite as a main component was obtained in the same manner as in Example 1.

Subsequently, 193.6 g of a transparent and colorless liquid was obtained by using the solution 1 in the same manner as in the synthesis of the compound 1 except that 70.3 g (0.48 moles) of n-butanol was used instead of the dibutyl(1-hydroxy-1-methylethyl)phosphonate.

The liquid obtained was analyzed by gas chromatography, and the result thereof was compared with gas chromatographic analysis results of cyclic phosphoric acid esters having known cyclic structures to confirm that the main component of the liquid obtained was the following cyclic phosphoric acid ester. The cyclic phosphoric acid ester was measured for the chlorine content by the method to be described later.

Table 2 shows the results obtained.

Cyclic Phosphoric Acid Ester C

Example 8

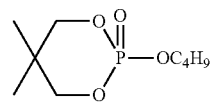

[Formula 8]

Example 9

A solution 1' containing neopentylenephosphorus chloridite as a main component was obtained in the same manner as in Example 1 except that chlorobenzene was used instead of the toluene.

Subsequently, 164.1 g of white powder was obtained by using the solution 1' in the same manner as in the synthesis of the compound 1 except that 43.2 g (0.48 moles) of 1,4-butanediol was used instead of the dibutyl(1-hydroxy-1-methylethyl)phosphonate.

The powder obtained was analyzed by gas chromatography, and the result thereof was compared with gas chromatographic analysis results of cyclic phosphoric acid esters having known cyclic structures to confirm that the main component of the powder obtained was the following cyclic phosphoric acid ester. The cyclic phosphoric acid ester was measured for the chlorine content by the method to be described later.

Table 2 shows the results obtained.

Cyclic Phosphoric Acid Ester D

Example 9

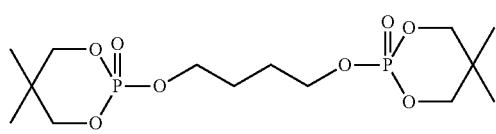

[Formula 9]

Example 10

A solution 1 containing neopentylenephosphorus chloridite as a main component was obtained in the same manner as in Example 1.

Subsequently, 288.3 g of white powder was obtained by using the solution 1 in the same manner as in the synthesis of the compound 1 except that 161.7 g (0.95 moles) of o-phenylphenol was used instead of the dibutyl(1-hydroxy-1-methylethyl)phosphonate.

The powder obtained was analyzed by gas chromatography, and the result thereof was compared with gas chromatographic analysis results of cyclic phosphoric acid esters having known cyclic structures to confirm that the main component of the powder obtained was the following cyclic phosphoric acid ester. The cyclic phosphoric acid ester was measured for the chlorine content by the method to be described later.

Table 2 shows the results obtained.

Cyclic Phosphoric Acid Ester E

Example 10

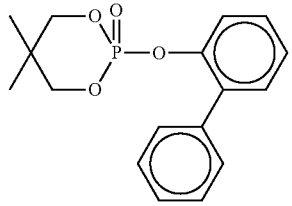

[Formula 10]

Comparative Example 10

A transparent and colorless liquid in an amount of 191.2 g containing the cyclic phosphoric acid ester C as a main component was obtained in the same manner as in Example 8 except that the solution 1C of Comparative Example 1 was used instead of the solution 1, and the liquid was measured for the chlorine content by the method to be described later.

Table 2 shows the results obtained.

Comparative Example 11

A solution 1C' containing neopentylenephosphorus chloridite as a main component was obtained in the same manner as in Comparative Example 1 except that chlorobenzene was used instead of the toluene.

Subsequently, 166.7 g of white powder containing the cyclic phosphoric acid ester D as a main component was obtained in the same manner as in Example 9 except that the solution 1C was used instead of the solution 1, and the powder was measured for the chlorine content by the method to be described later.

Table 2 shows the results obtained.

Comparative Example 12

White powder in an amount of 292.6 g containing the cyclic phosphoric acid ester E as a main component was obtained in the same manner as in Example 10 except that the solution 1C of Comparative Example 1 was used instead of the solution 1, and the powder was measured for the chlorine content by the method to be described later.

Table 2 shows the results obtained.

TABLE 2

| | Example 8 | Example 9 | Example 10 | Comparative Example 10 | Comparative Example 11 | Comparative Example 12 |
|---|---|---|---|---|---|---|
| Alkylene glycol compound (II) | Neopentyl glycol | Neopentyl glycol | Neopentyl glycol | Neopentyl glycol | Neopentyl glycol | Neopentyl glycol |
| Phosphorus trihalide(III) | Phosphorus trichloride | Phosphorus trichloride | Phosphorus trichloride | Phosphorus trichloride | Phosphorus trichloride | Phosphorus trichloride |
| Compound having hydroxyl group (V) | Butanol | 1,4-butanediol | o-phenyl phenol | Butanol | 1,4-butanediol | o-phenyl phenol |
| Chlorine content of compound (ppm) | 280 | 450 | 310 | 800 | 3800 | 790 |

The results of Examples 8 to 10, and Comparative Examples 1 and 10 to 12 reveal that the production process of the present invention allows production of a desired cyclic phosphoric acid ester having an extremely low halogen content.

Example 11

To a 2500-liter reaction vessel equipped with a stirrer, a thermometer, a thermostat, a powder addition device, a hydrochloric-acid-recovering device (condenser connected with a water scrubber) and a reflux condenser, 889 kg (6.47 kilomoles, exceeding neopentyl glycol by 4 mole %) of phosphorus trichloride as a phosphorus trihalide and 850 kg of toluene as a solvent were put in. The mixed solution was cooled to a temperature of 15° C. in the thermostat under a nitrogen atmosphere, and 650 kg (6.25 kilomoles) of neopentyl glycol as an alkylene glycol compound was gradually added thereto over 6 hours by using the powder addition device under stirring at 15 to 20° C. After completion of the addition, the resulting mixed solution was stirred and reacted in the same condition (under a nitrogen atmosphere at a temperature of 15 to 20° C.) for 2 hours to recover 433 kg of hydrogen chloride (hydrochloric acid gas) generated by using the hydrochloric-acid-recovering device. Thereafter, the resulting reaction mixture was heated to a temperature of 40° C., the pressure in the reaction vessel was reduced to 150 torr (20 kPa), and residual hydrogen chloride was removed under stirring for 2 hours in the same condition to obtain a solution 11 containing neopentylenephosphorus chloridite as a main component.

The solution 11 obtained was used to synthesize a compound 1 described above, and the compound obtained was measured for the chlorine content and the purity of the cyclic phosphoric acid ester by the method to be described later.

Table 3 shows the results obtained together with the materials and the reaction conditions.

In Table 3, the ratio of the phosphorus trihalide (III) to use to the alkylene glycol compound (II) is shown as "molar ratio".

Comparative Example 13

To a 2500-liter reaction vessel equipped with a stirrer, a thermometer, a thermostat, a dropping device, a hydrochloric-acid-recovering device (condenser connected with a water scrubber) and a reflux condenser, 650 kg (6.25 kilomoles) of neopentyl glycol as an alkylene glycol compound and 845 kg of toluene as a solvent were put in. The mixed solution was cooled to a temperature of 5° C. in the thermostat under a nitrogen atmosphere, and 859 kg (6.25 kilomoles, equimolar to neopentyl glycol) of phosphorus trichloride as a phosphorus trihalide was gradually added thereto over 10 hours by using the dropping device under stirring at 5 to 10° C. After completion of the addition, the resulting mixed solution was stirred and reacted in the same condition (under a nitrogen atmosphere at a temperature of 5 to 10° C.) for 2 hours to recover 437 kg of hydrogen chloride (hydrochloric acid gas) generated by using the hydrochloric-acid-recovering device. Thereafter, the resulting reaction solution was heated to a temperature of 60° C., the pressure in the reaction vessel was reduced to 150 torr (20 kPa), and residual hydrogen chloride was removed under stirring for 3 hours in the same condition to obtain a solution 13C containing neopentylenephosphorus chloridite as a main component.

The solution 13C obtained was used to synthesize a compound 1 described above, and the compound obtained was measured for the chlorine content and the purity of the cyclic phosphoric acid ester by the method to be described later.

Table 3 shows the results obtained together with the materials and the reaction conditions.

TABLE 3

| | Example 11 | Comparative Example 13 |
|---|---|---|
| Alkylene glycol compound (II) | Neopentyl glycol | Neopentyl glycol |
| Phosphorus trihalide(III) | Phosphorus trichloride | Phosphorus trichloride |
| Way of addition | Alkylene glycol compound was added. | Phosphorus trichloride was added. |
| Molar ratio of phosphorus trihalide used (to compound (II)) | 1.04 | 1.00 |
| Time period of addition (hours) | 6 | 10 |
| Reaction temperature (° C.) | 15~20 | 5~10 |
| Amount of compound 1 obtained (g) | 342.4 | 342.4 |
| Purity of cyclic phosphoric acid ester (%) | 94.2 | 89.5 |
| Halogen content of compound 1 (ppm) | 600 | 1700 |

(Measurement for Purity of Cyclic Phosphoric Acid Ester)

Each compound being measured was analyzed by gas chromatography with the device and in the conditions mentioned below and the result thereof was compared with gas chromatographic analysis results of known cyclic phosphoric acid esters to identify each cyclic phosphoric acid ester, and the area % of the phosphoric acid ester in the gas chromatography was determined as the purity of the cyclic ester.

Device: product by SHIMADZU CORPORATION, Model: GC-17A
Column: DB-1 (product by Agilent)
Length 30 m, I.D. 0.32 mm, Film 0.25 μm
Temperature: INJ 200° C., DET 250° C.
COL 35° C. 5 min→10° C./min→
200° C. 25 min hold→10° C./min→250° C.

(Measurement for Chlorine Content of Compound)

Each compound being measured was decomposed with metallic sodium in n-butanol and measured for the chlorine content (ppm) by potentiometric titration with a silver nitrate aqueous solution by using a potentiometric titrator (model: COM-2000, product by Hiranuma Sangyo Co., Ltd.)

The invention claimed is:
1. A process for producing a cyclic phosphoric acid ester comprising:
reacting a cyclic alkylene phosphorohalidite represented by formula (I):

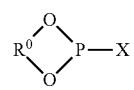

(I)

wherein $R^0$ is a linear or branched alkylene group having 2 to 20 carbon atoms or a cyclic alkylene group having 3 to 20 carbon atoms, and X is a halogen atom,
with a compound having a hydroxyl group represented by formula (V):

(V)

wherein n is an integer from 1 to 4, and R is an aliphatic residue having 1 to 8 carbon atoms or an aromatic residue having 6 to 18 carbon atoms that may have a substituent and that is represented by the following formula:

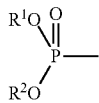

wherein $R^1$ and $R^2$ are each independently a linear alkyl group having 1 to 8 carbon atoms or a branched alkyl group having 3 to 8 carbon atoms, a cycloalkyl group having 3 to 8 carbon atoms, or an aryl group having 6 to 12 carbon atoms that may be substituted with a linear alkyl group having 1 to 4 carbon atoms or a branched alkyl group having 3 to 4 carbon atoms; or alternatively, $R^1$ and $R^2$, together with the oxygen atoms and the phosphorus atom to which they are attached, constitute a ring structure to obtain a reaction product represented by formula (VI):

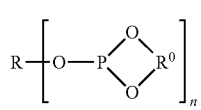 (VI)

wherein $R^0$, R and n are as defined above; and
oxidizing the reaction product to obtain a cyclic phosphoric acid ester represented by formula (VII):

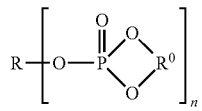 (VII)

wherein $R^0$, R and n are as defined above; and
wherein the cyclic alkylene phosphorohalidite of formula (I) is obtained by reacting an alkylene glycol compound represented by formula (II):

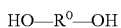 (II)

wherein $R^0$ is as defined above,
with a phosphorus trihalide represented by formula (III):

 (III)

wherein X is as defined above,
wherein the phosphorus trihalide and the alkylene glycol compound are reacted under conditions where the phosphorus trihalide is present in an excess amount relative to the amount of the alkylene glycol compound in the reaction system,
wherein the compound having a hydroxyl group of formula (V) is ethanol, propanol, butanol, phenol, cresol, xylenol, phenylphenol, dibutyl(1-hydroxy-1-methylethyl) phosphonate, dibutylhydroxymethylphosphonate, ethylene glycol, 1,3-propanediol or 1,4-butanediol.

2. The process for producing a cyclic phosphoric acid ester of claim 1, wherein the cyclic phosphoric acid ester of formula (VII) has a purity of more than 90.0% and a halogen content of 750 ppm or less.

3. The process for producing a cyclic phosphoric acid ester of claim 1, wherein the cyclic phosphoric acid ester of formula (VII) is

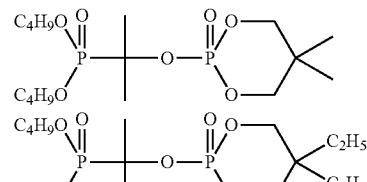

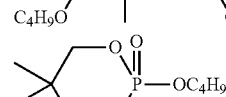

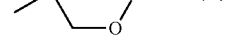

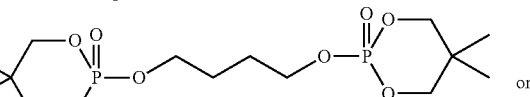

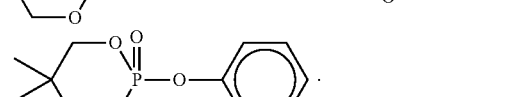

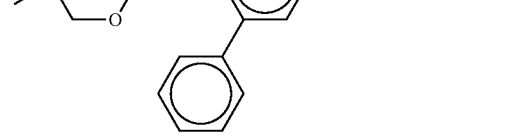 or

or

4. The process for producing a cyclic phosphoric acid ester of claim 1, wherein the reaction of the phosphorus trihalide of formula (III) and the alkylene glycol compound of formula (II) comprises: adding the whole amount of the phosphorus trihalide to use to the reaction system; and then gradually adding the alkylene glycol compound thereto.

5. The process for producing a cyclic phosphoric acid ester of claim 1, wherein the phosphorus trihalide of formula (III) is used at a proportion of 0.99 to 1.15 moles with respect to 1 mole of the alkylene glycol compound of formula (II).

6. The process for producing a cyclic phosphoric acid ester of claim 1, wherein the reaction of the phosphorus trihalide of formula (III) and the alkylene glycol compound of formula (II) is carried out at a temperature in a range of −5° C. to 60° C.

7. The process for producing a cyclic phosphoric acid ester of claim 1, wherein the alkylene glycol compound of formula (II) is a 1,3-propanediol compound represented by formula (IV):

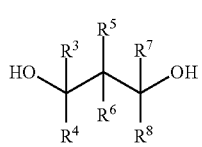 (IV)

wherein $R^3$, $R^4$, $R^5$, $R^6$, $R^7$ and $R^8$ are each independently a hydrogen atom, or a linear alkyl group having 1 to 5 carbon atoms or a branched alkyl group having 3 to 5 carbon atoms.

8. The process for producing a cyclic phosphoric acid ester of claim 1, wherein the alkylene glycol compound of formula (II) is neopentyl glycol or 2-butyl-2-ethyl-1,3-propanediol.

9. The process for producing a cyclic phosphoric acid ester of claim 1, wherein the phosphorus trihalide of formula (III) is phosphorus trichloride or phosphorus tribromide.

* * * * *